(12) United States Patent
Yamashita et al.

(10) Patent No.: US 9,723,999 B2
(45) Date of Patent: Aug. 8, 2017

(54) ELECTRONIC BLOOD PRESSURE METER

(71) Applicant: OMRON HEALTHCARE Co., Ltd., Kyoto (JP)

(72) Inventors: Yuki Yamashita, Kyoto (JP); Tatsuya Kobayashi, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 47 days.

(21) Appl. No.: 14/353,328

(22) PCT Filed: Oct. 5, 2012

(86) PCT No.: PCT/JP2012/075939
§ 371 (c)(1),
(2) Date: Apr. 22, 2014

(87) PCT Pub. No.: WO2013/084579
PCT Pub. Date: Jun. 13, 2013

(65) Prior Publication Data
US 2014/0276146 A1  Sep. 18, 2014

(30) Foreign Application Priority Data
Dec. 9, 2011  (JP) .................................. 2011-269908

(51) Int. Cl.
*A61B 5/02* (2006.01)
*A61B 5/022* (2006.01)
(Continued)

(52) U.S. Cl.
CPC ........ *A61B 5/02225* (2013.01); *A61B 5/0225* (2013.01); *A61B 5/02233* (2013.01);
(Continued)

(58) Field of Classification Search
CPC ......... A61B 5/02; A61B 5/021; H01L 41/042; F04B 43/046
(Continued)

(56) References Cited

U.S. PATENT DOCUMENTS 4,479,494 A * 10/1984 McEwen ............ A61B 5/02141
600/495
5,920,221 A * 7/1999 Shen et al. ..................... 327/264
(Continued)

FOREIGN PATENT DOCUMENTS

CN  100376297 C  3/2008
JP  64-19184 A  1/1989
(Continued)

OTHER PUBLICATIONS

CurieJet, Piezoelectric Micropump Animation, 2010 Microjet Technology Co., Ltd.*
(Continued)

*Primary Examiner* — Jacqueline Cheng
*Assistant Examiner* — Puya Agahi
(74) *Attorney, Agent, or Firm* — Osha Liang LLP

(57) ABSTRACT

An electronic blood pressure meter includes a cuff that is to be worn on a measurement area, a piezoelectric pump that adjusts a pressure applied to the cuff, a drive circuit that drives the piezoelectric pump, and a controller that outputs, to the drive circuit, a pulse signal defining a driving timing of the piezoelectric pump. The drive circuit includes a switching circuit for switching a connection relationship between respective voltages applied to both ends of the piezoelectric pump in response to corresponding first and second driving signals, and a signal generation circuit that outputs the first and second driving signals based on the pulse signal outputted from the controller. The signal generation circuit has a signal conditioning circuit that adjusts
(Continued)

timings of the first and second driving signals so that the phases of the first and second driving signals do not overlap.

2 Claims, 9 Drawing Sheets

(51) Int. Cl.
    *H01L 41/04*     (2006.01)
    *A61B 5/0225*     (2006.01)
    *H02H 9/00*     (2006.01)

(52) U.S. Cl.
    CPC ........ *A61B 5/02255* (2013.01); *H01L 41/042* (2013.01); *H02H 9/001* (2013.01); *H02H 9/002* (2013.01)

(58) Field of Classification Search
    USPC ............. 600/481, 490–499; 338/2, 4, 36, 47
    See application file for complete search history.

(56) References Cited

U.S. PATENT DOCUMENTS

| | | | | |
|---|---|---|---|---|
| 5,980,248 | A * | 11/1999 | Kusakabe | A61C 1/0007 |
| | | | | 433/131 |
| 6,164,933 | A * | 12/2000 | Tani et al. | 417/413.2 |
| 2004/0079360 | A1* | 4/2004 | Coffee et al. | 128/200.14 |
| 2006/0067601 | A1* | 3/2006 | Tateishi | G02F 1/0121 |
| | | | | 385/3 |
| 2007/0252565 | A1* | 11/2007 | Wang | G05F 1/573 |
| | | | | 323/277 |
| 2009/0007685 | A1* | 1/2009 | Cheng | G01B 7/18 |
| | | | | 73/774 |
| 2009/0045696 | A1* | 2/2009 | Suzuki | 310/317 |
| 2009/0060750 | A1* | 3/2009 | Chen et al. | 417/26 |
| 2009/0167109 | A1* | 7/2009 | Tomita et al. | 310/317 |
| 2009/0206699 | A1* | 8/2009 | Osano | 310/317 |
| 2009/0243431 | A1* | 10/2009 | Ohsawa | 310/317 |

FOREIGN PATENT DOCUMENTS

| | | | |
|---|---|---|---|
| JP | 7-27053 A | | 1/1995 |
| JP | 2001-65461 A | | 3/2001 |
| JP | 2009-74418 A | | 4/2009 |
| JP | 200974418 a | * | 4/2009 |
| JP | 2010-19182 A | | 1/2010 |

OTHER PUBLICATIONS

International Search Report for corresponding International Application No. PCT/JP2012/075939, mailed Oct. 30, 2012 (4 pages).

Written Opinion for corresponding International Application No. PCT/JP2012/075939, mailed Oct. 30, 2012 (7 pages).

Office Action issued in corresponding Chinese Application No. 201280060118.2 dated Apr. 27, 2015, and English translation thereof (13 pages).

* cited by examiner

ELECTRONIC BLOOD PRESSURE METER

TECHNICAL FIELD

This invention relates to electronic blood pressure meters, and particularly relates to electronic blood pressure meters that measure blood pressure by, for example, inflating an air bladder using a piezoelectric pump.

BACKGROUND ART

Blood pressure is one index for analyzing cardiovascular disease. Performing a risk analysis for cardiovascular disease based on blood pressure is effective in preventing cardiovascular-related conditions such as stroke, heart failure, and myocardial infarction. In particular, morning hypertension, in which the blood pressure rises in the early morning, is related to heart disease, stroke, and the like. Furthermore, among morning hypertension symptoms, the symptom called "morning surge", in which the blood pressure rapidly rises within one hour to one and a half hours after waking up, has been found to have a causal relationship with stroke. Accordingly, understanding the interrelationship between time (lifestyle) and changes in blood pressure is useful in risk analysis for cardiovascular-related conditions. It is therefore necessary to continuously measure blood pressure over a long period of time.

Furthermore, recent study results have shown that home blood pressure, which is blood pressure measured at home, is more effective in the prevention, diagnosis, treatment, and so on of cardiovascular-related conditions than blood pressure measured at a hospital or during a health examination (casual blood pressure). Accordingly, blood pressure meters for home use have become widely prevalent, and home blood pressure values have started to become used in diagnoses; thus various types of blood pressure meters for home use have been produced.

In a typical electronic blood pressure meter, a manchette containing an air bladder is uniformly wrapped around a part of a body, and changes in the volume of an arterial vessel pressurized by inflating/deflating the air bladder with air is obtained as changes in the amplitude of the pressure in the air bladder (a cuff pressure); meanwhile, electronic blood pressure meters that employ an oscillometric method for calculating blood pressure are in use, and the air bladder can be inflated using a piezoelectric pump, as disclosed in JP 2009-74418A, for example.

CITATION LIST

Patent Literature

Patent Literature 1: JP 2009-74418A

SUMMARY OF INVENTION

Technical Problem

Meanwhile, an external drive technique and a self-oscillating technique can be given as techniques for driving a piezoelectric pump, and with the self-oscillating technique, it is necessary to make fine adjustments to the output properties of a pulse due to design error or the like in the circuit; however, there is a problem in that when a circuit for making such fine adjustments is provided, the circuitry layout and so on increases in size.

The external drive technique only requires that, for example, a pulse matching the properties of the piezoelectric pump be outputted from the CPU, and thus is easy to incorporate into designs. A technique where the pulse is applied to the piezoelectric pump using an H-bridge circuit or the like is employed. It is known that the signal inverts when the H-bridge circuit switches, and a high inrush current will be produced in response to the input of a signal inverted relative to a charge that has built up in the piezoelectric pump.

The inrush current causes a drop in a battery cell voltage, which in turn can affect the accuracy of blood pressure measurement. There is also a problem of a shorter lifespan of the battery in the blood pressure meter.

Having been achieved to solve such problems, it is an object of the present invention to provide an electronic blood pressure meter capable of suppressing inrush current using a simple configuration.

Solution to Problem

An electronic blood pressure meter according to an aspect of the present invention includes a cuff that is to be worn on a measurement area, a piezoelectric pump that adjusts a pressure applied to the cuff, a drive circuit that drives the piezoelectric pump, and a controller that outputs, to the drive circuit, a pulse signal defining a driving timing of the piezoelectric pump. The drive circuit includes a switching circuit for switching a connection relationship between respective voltages applied to both ends of the piezoelectric pump in response to corresponding first and second driving signals, and a signal generation circuit that outputs the first and second driving signals based on the pulse signal outputted from the controller. The signal generation circuit has a signal conditioning circuit that adjusts timings of the first and second driving signals so that the phases of the first and second driving signals do not overlap.

Preferably, the signal generation circuit further includes an inverting circuit that outputs an inverted pulse signal obtained by inverting the pulse signal, and the signal conditioning circuit adjusts a duty ratio of at least one of the pulse signal and the inverted pulse signal.

In particular, preferably, the signal conditioning circuit has a delay circuit that delays the phase of a signal and a waveform shaping circuit.

In particular, preferably, the delay circuit is configured of a resistance element and a capacitance element.

In particular, preferably, the resistance element is a variable resistance element whose resistance value changes in accordance with an instruction from the exterior.

In particular, preferably, the capacitance element is a variable capacitance element whose capacitance component changes in accordance with an instruction from the exterior.

Advantageous Effects of Invention

The present invention makes it possible to suppress inrush current using a simple technique.

DESCRIPTION OF EMBODIMENTS

Figure 1:
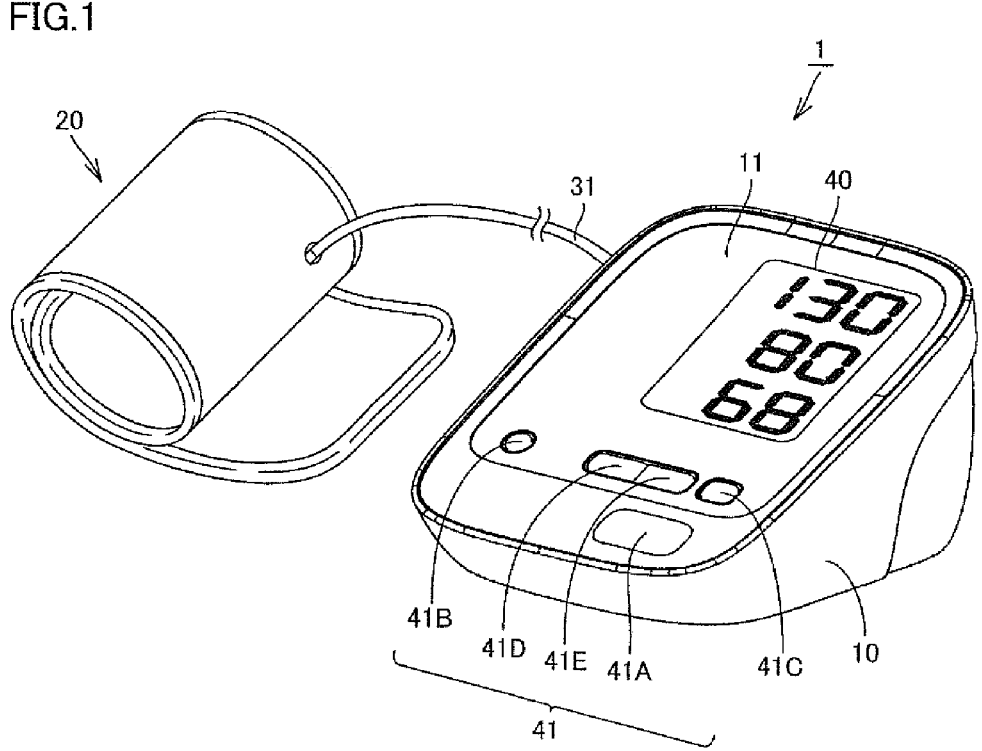
FIG. 1 is a diagram illustrating an external view of an electronic blood pressure meter 1 according to an embodiment of the present invention.

Hereinafter, an electronic blood pressure meter according to an embodiment of this invention will be described in detail with reference to the drawings. When numbers, amounts, and so on are discussed in the following embodiment, it should be noted that unless explicitly mentioned otherwise, the scope of the present invention is not necessarily limited to those numbers, amounts, and so on. Furthermore, in the case where multiple embodiments are given hereinafter, it is assumed from the outset that the configurations of the respective embodiments can be combined as appropriate unless explicitly mentioned otherwise. In the drawings, identical reference numerals refer to identical or corresponding elements; there are also cases where redundant descriptions are omitted.

The present embodiment describes an electronic blood pressure meter that calculates blood pressures through an oscillometric method using the upper arm as a measurement area, and as an example, includes a single pressure sensor. Note that the method applied for the blood pressure calculation is not limited to the oscillometric method. Note also that there may be a plurality of pressure sensors.

External View of Electronic Blood Pressure Meter 1

FIG. 1 is a diagram illustrating an external view of an electronic blood pressure meter 1 according to this embodiment of the present invention.

Figure 2:
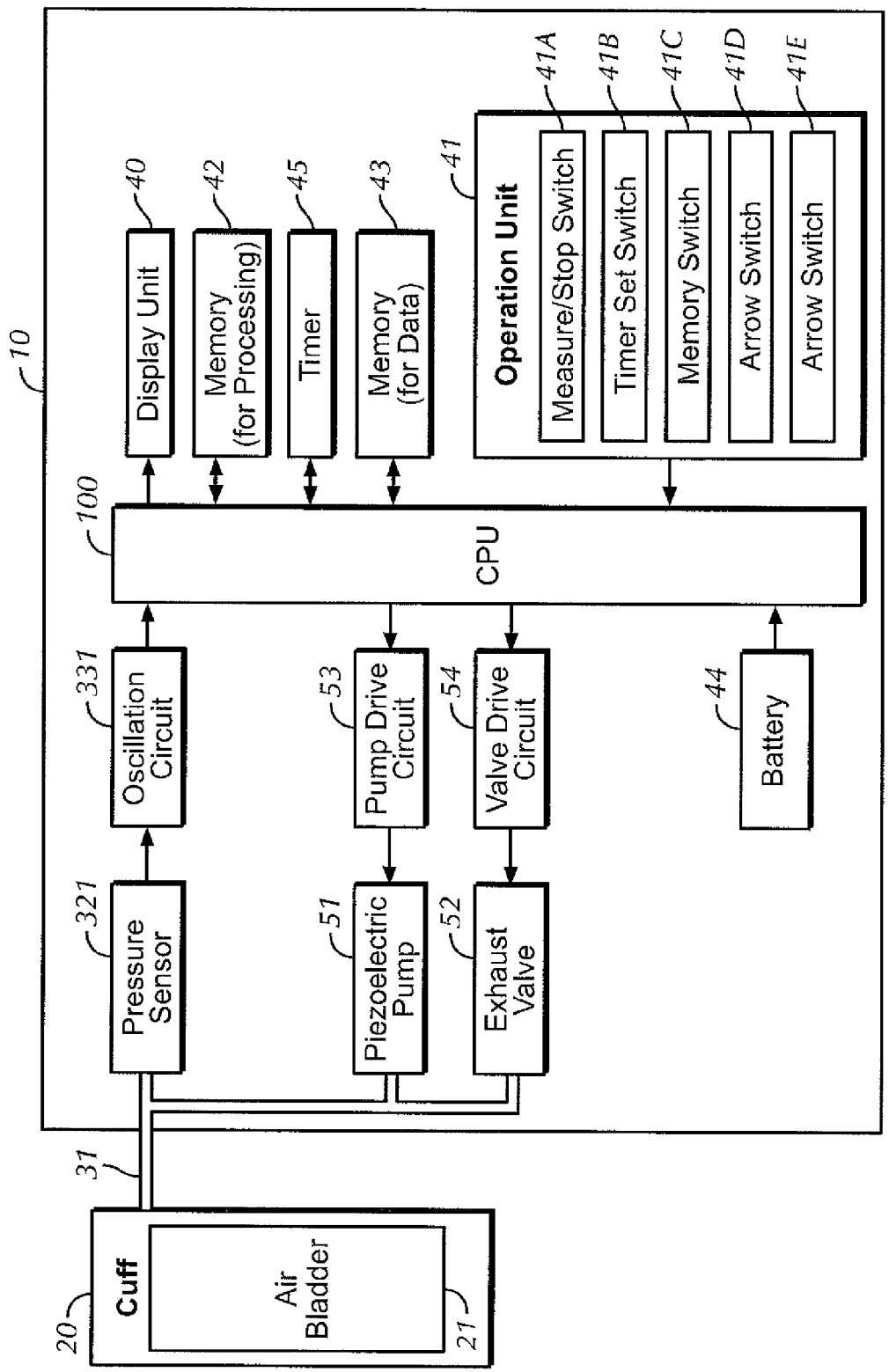
FIG. 2 is a block diagram illustrating the hardware configuration of an electronic blood pressure meter according to the embodiment of the present invention.

FIG. 2 is a block diagram illustrating the hardware configuration of the electronic blood pressure meter 1 according to this embodiment of the present invention.

As shown in FIGS. 1 and 2, the electronic blood pressure meter 1 includes a main body portion 10, a front cover 11, and a cuff 20 that can be wrapped around the upper arm of a measurement subject. The cuff 20 includes an air bladder 21. A display unit 40 configured of a liquid-crystal display or the like and an operation unit 41 configured of a plurality of switches for accepting instructions from a user (measurement subject) are disposed on the front cover 11.

In addition to the aforementioned display unit 40 and operation unit 41, the main body portion 10 includes: a CPU (central processing unit) 100 for carrying out centralized control of the respective elements and performing various types of computational processes; a processing memory 42 for storing programs, data, and so on for causing the CPU 100 to perform predetermined operations; a data storage memory 43 for storing measured blood pressure data and so on; a battery 44 for supplying power to the various elements of the main body portion 10; and a timer 45 that measures the current time and outputs measured time data to the CPU 100.

The operation unit 41 includes: a measure/stop switch 41A that accepts the input of an instruction for turning the power on or off and accepts an instruction for starting and stopping measurement; a timer set switch 41B manipulated in order to set the timer 45; a memory switch 41C for accepting an instruction to read out information stored in the memory 43, such as blood pressure data, from the memory 43 and display that information in the display unit 40; and arrow switches 41D and 41E for accepting instructions to raise/lower numbers when setting the timer and memory numbers when calling information from a memory.

The main body portion 10 further includes a cuff pressure adjustment mechanism having a piezoelectric pump 51 and an exhaust valve (called simply a "valve" hereinafter) 52. An air system configured of the piezoelectric pump 51, the valve 52, and a pressure sensor 321 for detecting a pressure within the air bladder 21 (a cuff pressure) is connected, via a cuff air tube 31, to the air bladder 21 enclosed within the cuff 20.

The main body portion 10 further includes the aforementioned air system, the cuff pressure adjustment mechanism, and an oscillation circuit 331. The cuff pressure adjustment mechanism includes a pump drive circuit 53 and a valve drive circuit 54, in addition to the piezoelectric pump 51 and the valve 52.

The piezoelectric pump 51 supplies air to the air bladder 21 in order to increase the cuff pressure. The valve 52 is opened/closed in order to discharge or inject air from or into the air bladder 21.

The pump drive circuit 53 controls the driving of the piezoelectric pump 51 based on a control signal (pulse signal) supplied from the CPU 100. The valve drive circuit 54 controls the opening/closing of the valve 52 based on a control signal supplied from the CPU 100.

An electrostatic capacitance pressure sensor, for example, is used for the pressure sensor 321. With an electrostatic capacitance pressure sensor, a capacity value changes in accordance with a detected cuff pressure. The oscillation circuit 331 is connected to the pressure sensor 321, and oscillates based on the capacity value of the pressure sensor. In the present embodiment, the oscillation circuit 331 operates in response to an instruction from the CPU 100; the CPU 100 outputs an activation signal to the oscillation circuit 331. Note that the pressure sensor is not limited to an electrostatic capacitance pressure sensor, and a different type may be used as well. For example, a piezoelectric resistance-based pressure sensor that uses a piezoelectric resistance element can also be employed.

The oscillation circuit 331 that has received the activation signal from the CPU 100 outputs a signal having a frequency that corresponds to the capacity value of the pressure sensor 321 (this will be called a "frequency signal" hereinafter). The outputted frequency signal is supplied to the CPU 100.

The CPU 100 detects a pressure by converting the frequency signal inputted from the oscillation circuit 331 into a pressure.

Figure 3:
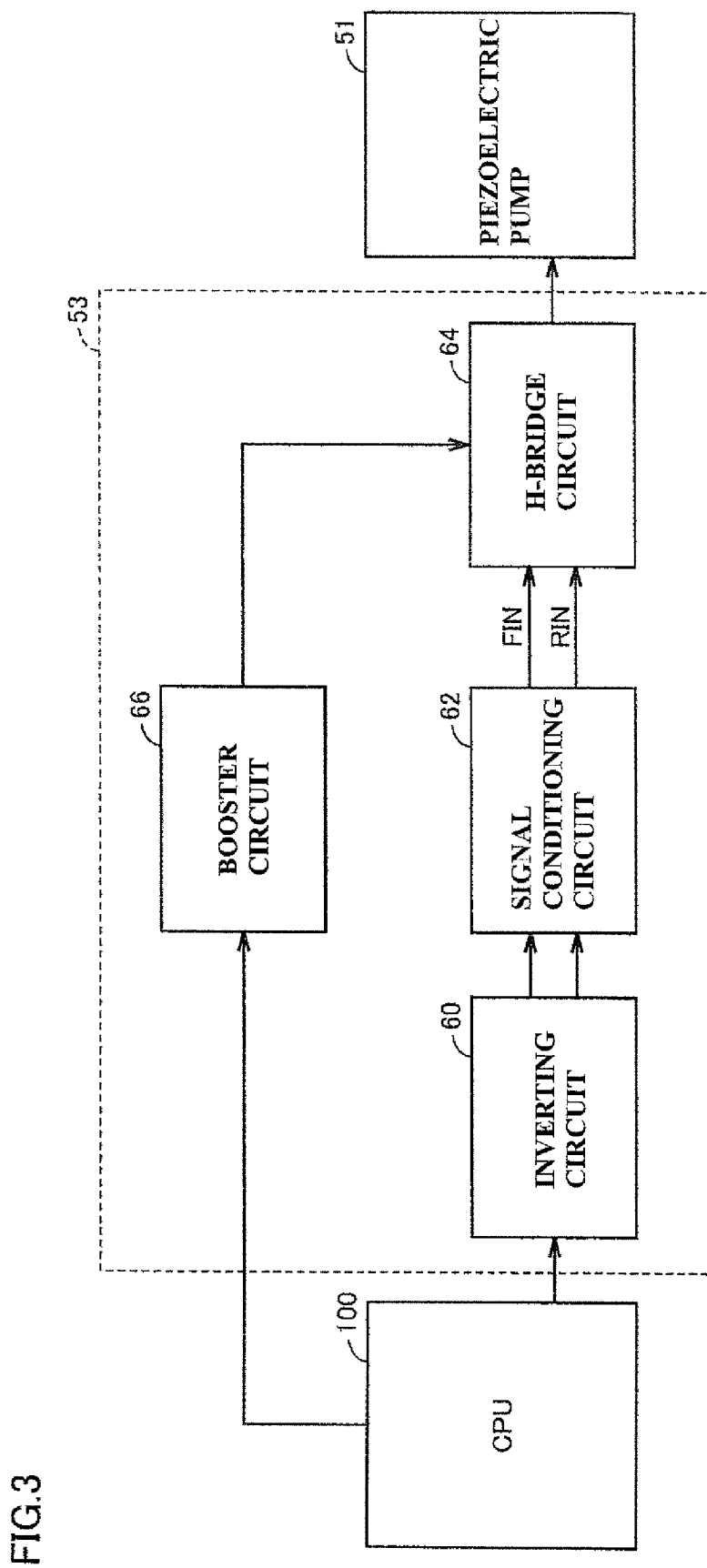
FIG. 3 is a diagram illustrating the configuration of a pump drive circuit 53 according to the embodiment of the present invention.

FIG. 3 is a diagram illustrating the configuration of the pump drive circuit 53 according to this embodiment of the present invention. As shown in FIG. 3, the pump drive circuit 53 includes an inverting circuit 60, a signal conditioning circuit 62, an H-bridge circuit 64, and a booster circuit 66.

The inverting circuit 60 accepts the input of a control signal (a pulse signal) supplied from the CPU 100. The control signal (pulse signal) is a timing signal for regulating the driving of the piezoelectric pump 51. Then, in response to the input of the control signal (pulse signal), the inverting circuit 60 outputs two control signals of its own. Specifically, one control signal is outputted as a signal having the same phase as the inputted pulse signal, whereas the other is outputted as an inverted pulse signal in which the phase of the pulse signal is inverted.

The signal conditioning circuit 62 accepts the pulse signal and the inverted pulse signal inputted from the inverting circuit 60, and outputs these signals as first and second driving signals for driving the H-bridge circuit 64. More specifically, the signal conditioning circuit 62 adjusts the duty ratio of at least one of the inputted pulse signal and the inverted pulse signal, and outputs the signals.

The H-bridge circuit 64 is a switching circuit that supplies a predetermined current to the piezoelectric pump 51, and supplies the predetermined current to the piezoelectric pump 51 in accordance with the first and second driving signals. In accordance with the first driving signal, the H-bridge circuit 64 applies a voltage to both ends of the piezoelectric pump 51 so that a first-direction (positive-direction) current is supplied to the piezoelectric pump 51. Likewise, in accordance with the second driving signal, the H-bridge circuit 64 applies a voltage to both ends of the piezoelectric pump 51 so that a second-direction (negative-direction; the opposite of the first direction) current is supplied to the piezoelectric pump 51. In other words, the H-bridge circuit 64 executes switching control that switches (alternates the logic of) the connection relationship of the voltages applied to the respective ends of the piezoelectric pump 51 in accordance with the first and second driving signals. Specifically, one of the voltages applied to the piezoelectric pump 51 is a high voltage and the other a low voltage, and the connection relationship of the voltages is switched in accordance with the first and second driving signals.

The booster circuit 66 adjusts the level of an applied voltage supplied to the H-bridge circuit 64 in accordance with an instruction from the CPU 100. The amount of current flowing in the piezoelectric pump 51 can be adjusted by adjusting the level of the applied voltage. Note that in the case where the amount of current flowing in the piezoelectric pump 51 is constant, it is not necessary for the CPU 100 to instruct the voltage to be adjusted, and the booster circuit 66 may simply boost the voltage to a desired fixed voltage and supply that voltage to the H-bridge circuit 64. Of course, if it is not necessary to boost the voltage, a configuration in which the booster circuit 66 is not provided may be employed. Note that the configurations of the H-bridge circuit 64 and the booster circuit 66 are already known and thus detailed descriptions thereof will not be given.

Figure 4:
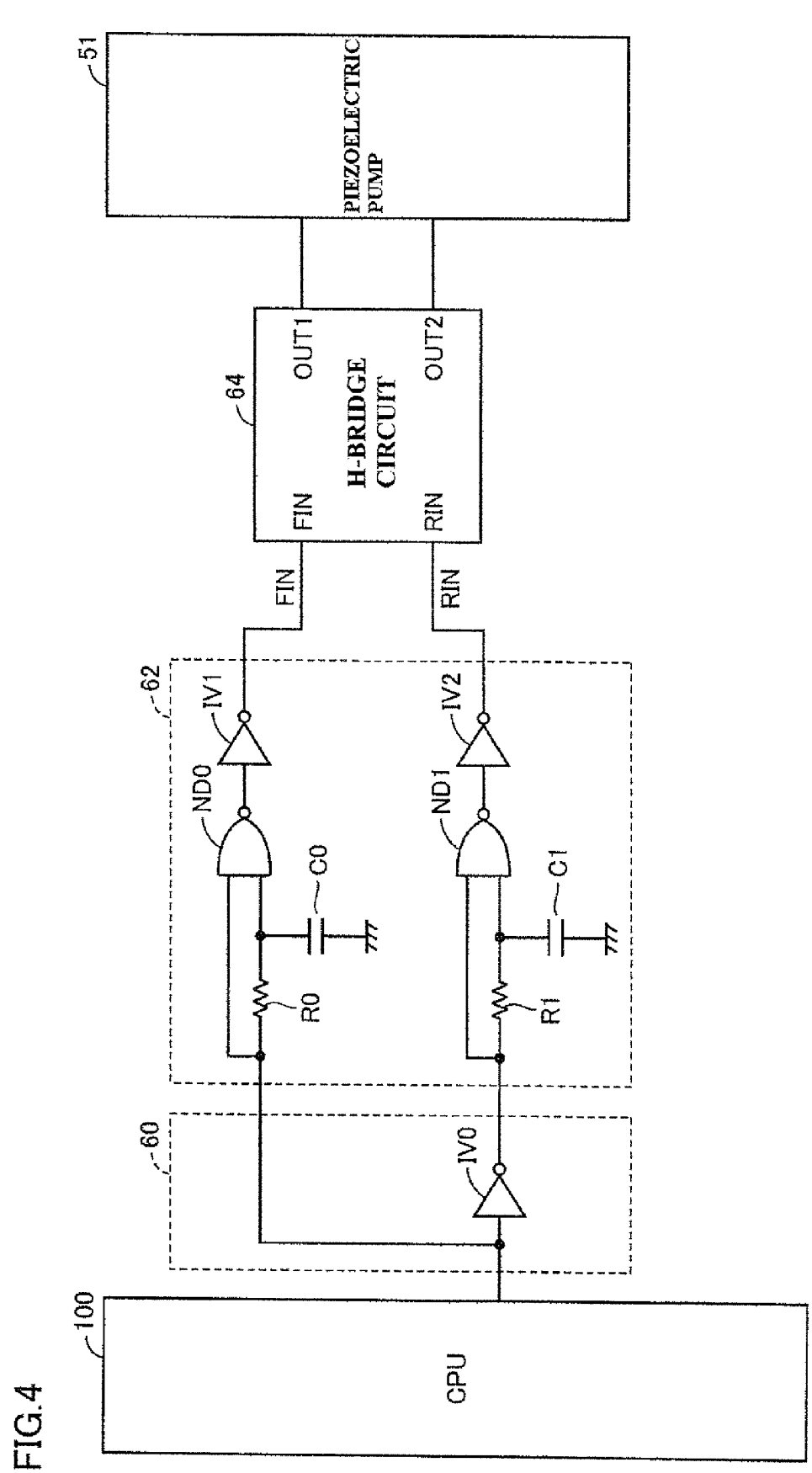
FIG. 4 is a diagram illustrating in detail the configuration of an inverting circuit 60 and a signal conditioning circuit 62 according to the embodiment of the present invention.

FIG. 4 is a diagram illustrating in detail the configuration of the inverting circuit 60 and the signal conditioning circuit 62 according to this embodiment of the present invention.

As shown in FIG. 4, the inverting circuit 60 includes an inverter IV0. The pulse signal inputted into the inverting circuit 60 branches, with one branch being outputted directly to the signal conditioning circuit 62 and the other branch being outputted to the signal conditioning circuit 62 via the inverter IV0 as the inverted pulse signal.

The signal conditioning circuit 62 includes inverters IV1 and IV2, NAND circuits ND0 and ND1, resistance elements R0 and R1, and capacitance elements C0 and C1.

One input node in the NAND circuit ND0 accepts the input of the pulse signal, whereas the other input node accepts the input of the pulse signal that has been passed through a low-pass filter. The low-pass filter is configured of the resistance element R0 and the capacitance element C0. The rise and fall of the pulse signal that has passed through the low-pass filter are smoothed according to the resistance and capacitance components of the resistance element R0 and the capacitance element C0.

The NAND circuit ND0 outputs an L level when both input nodes go to H level, and an H level signal is then outputted from the signal conditioning circuit 62 via the inverter IV1.

Here, because the rise to H level and the fall to L level of the signal passing through the low-pass filter are smoothed, the phase of the signal within the NAND circuit ND0 is delayed. As a result, the timing of the rise and fall of the signal outputted from the NAND circuit ND0 changes. In other words, the duty ratio of the signal outputted from the NAND circuit ND0 can be adjusted, and as a result, the duty ratio of the signal outputted from the signal conditioning circuit 62 is adjusted as well.

In a similar manner, one input node in the NAND circuit ND1 accepts the input of the inverted pulse signal, whereas the other input node accepts the input of the inverted pulse signal that has passed through a low-pass filter. The low-pass filter is configured of the resistance element R1 and the capacitance element C1. The rise and fall of the inverted pulse signal that has passed through the low-pass filter are smoothed according to the resistance and capacitance components of the resistance element R1 and the capacitance element C1.

The NAND circuit ND1 outputs an L level when both input nodes go to H level, and an H level signal is then outputted from the signal conditioning circuit 62 via the inverter IV2.

Here, because the rise to H level and the fall to L level of the signal passing through the low-pass filter are smoothed, the phase of the signal within the NAND circuit ND1 is delayed. As a result, the timing of the rise and fall of the signal outputted from the NAND circuit ND1 changes. In other words, the duty ratio of the signal outputted from the NAND circuit ND1 can be adjusted, and as a result, the duty ratio of the signal outputted from the signal conditioning circuit 62 is adjusted as well.

Figure 5:
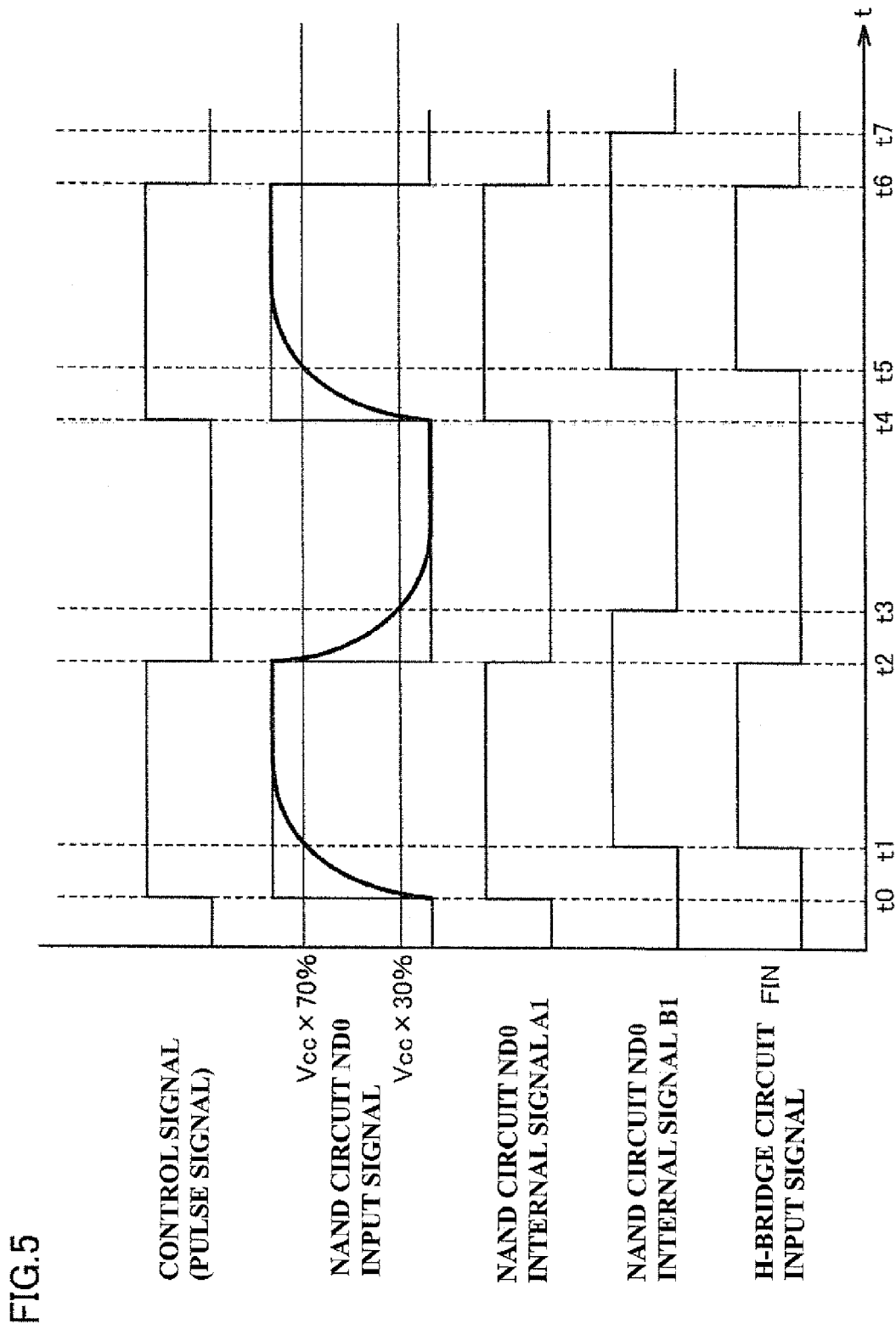
FIG. 5 is a diagram illustrating input and output signal waveforms of the inverting circuit 60 and the signal conditioning circuit 62 according to the embodiment of the present invention.

FIG. 5 is a diagram illustrating input and output signal waveforms of the inverting circuit 60 and the signal conditioning circuit 62 according to this embodiment of the present invention.

FIG. 5 illustrates a case where a control signal having a set cycle (a pulse signal) is outputted from the CPU 100. Specifically, FIG. 5 illustrates a case where the signal changes to H level at a time t0, to L level at a time t2, to H level at a time t4, and to L level at a time t6.

FIG. 5 also shows the waveform of the signal inputted into the NAND circuit ND0 in accordance with the stated control signal. In the present embodiment, it is assumed that the amplitude of the inputted signal waveform is 0–Vcc, and the waveform is shaped within the NAND circuit ND0 so that 30% or less of the maximum amplitude is taken as L level and 70% or greater of the maximum amplitude is taken as H level.

Here, a signal having the same phase as the pulse signal is inputted into one of the input nodes in the NAND circuit ND0 because there is no delay. In other words, because there is no delay, the rise and fall of an internal signal A1 that follows the signal from the one input node in the NAND circuit ND0 goes to H level at the time t0, to L level at the time t2, the H level at the time t4, and to L level at the time t6, in the same phase as the control signal.

On the other hand, the signal that has passed through the low-pass filter is inputted into the other input node in the NAND circuit ND0, and thus a signal having a waveform in which the rise and fall of the signal have been smoothed is inputted. In other words, because there is delay, the rise and fall of an internal signal B1 that follows the signal from the other input node in the NAND circuit ND0 goes to H level at a time t1, to L level at a time t3, to H level at a time t5, and to L level at a time t7, with the phase being delayed from that of the control signal.

The signal outputted from the NAND circuit ND0 is outputted based on a combination of the internal signals A1 and B1. Specifically, an H level signal is outputted in the case where one of the internal signals A1 and B1 is L level, whereas an L level signal is outputted in the case where both the internal signals A1 and B1 are H level.

In the present embodiment, the inverted signal from the inverter IV1 (that is, the signal inputted into the H-bridge circuit (the driving signal FIN)) goes to H level at the time t1, to L level at the time t2, to H level at the time t5, and to L level at the time t6.

Through this, the signal conditioning circuit 62 outputs the driving signal FIN, obtained by adjusting the duty ratio of the control signal (pulse signal), for input into the H-bridge circuit.

Figure 6:
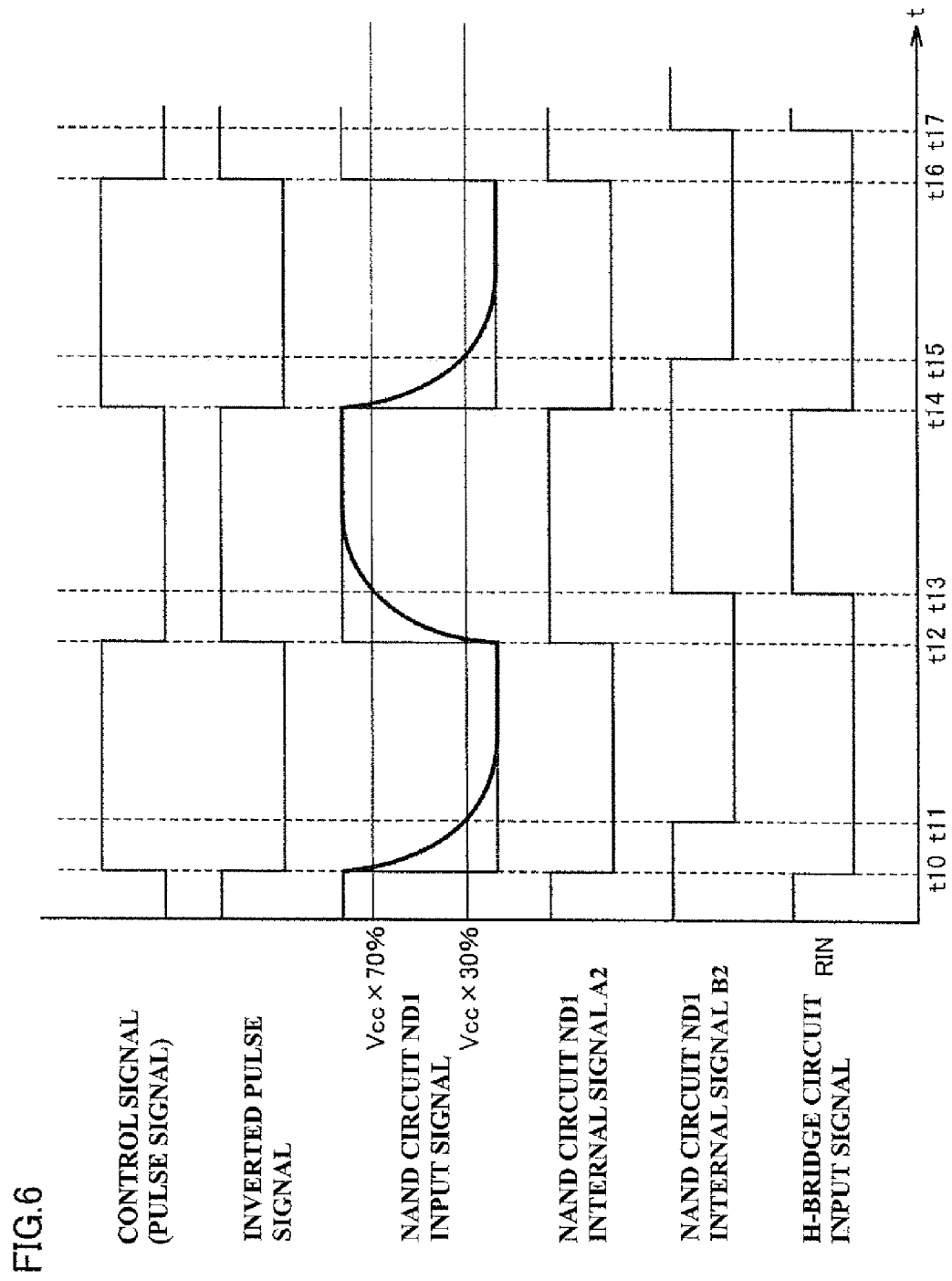
FIG. 6 is another diagram illustrating input and output signal waveforms of the inverting circuit 60 and the signal conditioning circuit 62 according to the embodiment of the present invention.

FIG. 6 is another diagram illustrating input and output signal waveforms of the inverting circuit 60 and the signal conditioning circuit 62 according to this embodiment of the present invention.

FIG. 6 illustrates a case where a control signal having a set cycle (a pulse signal) is outputted from the CPU 100.

Specifically, FIG. 6 illustrates a case where the signal changes to H level at a time t10, to L level at a time t12, to H level at a time t14, and to L level at a time t16.

FIG. 6 also shows the inverted pulse signal inverted by the inverter IV0.

Specifically, FIG. 6 illustrates a case where the signal changes to L level at the time t10, to H level at the time t12, to L level at the time t14, and to H level at the time t16.

FIG. 6 also shows the waveform of the signal inputted into the NAND circuit ND1 in accordance with the stated inverted pulse signal. In the present embodiment, it is assumed that the amplitude of the inputted signal waveform is 0–Vcc, and the waveform is shaped within the NAND circuit ND1 so that 30% or less of the maximum amplitude is taken as L level and 70% or greater of the maximum amplitude is taken as H level.

Here, a signal having the same phase as the inverted pulse signal is inputted into one of the input nodes in the NAND circuit ND1 because there is no delay. In other words, because there is no delay, the rise and fall of an internal signal A2 that follows the signal from the one input node in the NAND circuit ND1 goes to L level at the time t10, to H level at the time t12, the L level at the time t14, and to H level at the time t16, in the same phase as the inverted pulse signal.

On the other hand, the signal that has passed through the low-pass filter is inputted into the other input node in the NAND circuit ND1, and thus a signal having a waveform in which the rise and fall of the signal have been smoothed is inputted. In other words, because there is delay, the rise and fall of an internal signal B2 that follows the signal from the other input node in the NAND circuit ND1 goes to L level at a time t11, to H level at a time t13, to L level at a time t15, and to H level at a time t17, with the phase being delayed from that of the control signal.

The signal outputted from the NAND circuit ND1 is outputted based on a combination of the internal signals A2 and B2. Specifically, an H level signal is outputted in the case where one of the internal signals A2 and B2 is L level, whereas an L level signal is outputted in the case where both the internal signals A2 and B2 are H level.

In the present embodiment, the inverted signal from the inverter IV2 (that is, the signal inputted into the H-bridge circuit (the driving signal RIN)) goes to L level at the time t10, to H level at the time t13, to L level at the time t14, and to H level at the time t17.

Through this, the signal conditioning circuit 62 outputs the driving signal RIN, obtained by adjusting the duty ratio of the control signal (pulse signal), for input into the H-bridge circuit.

Figure 7:
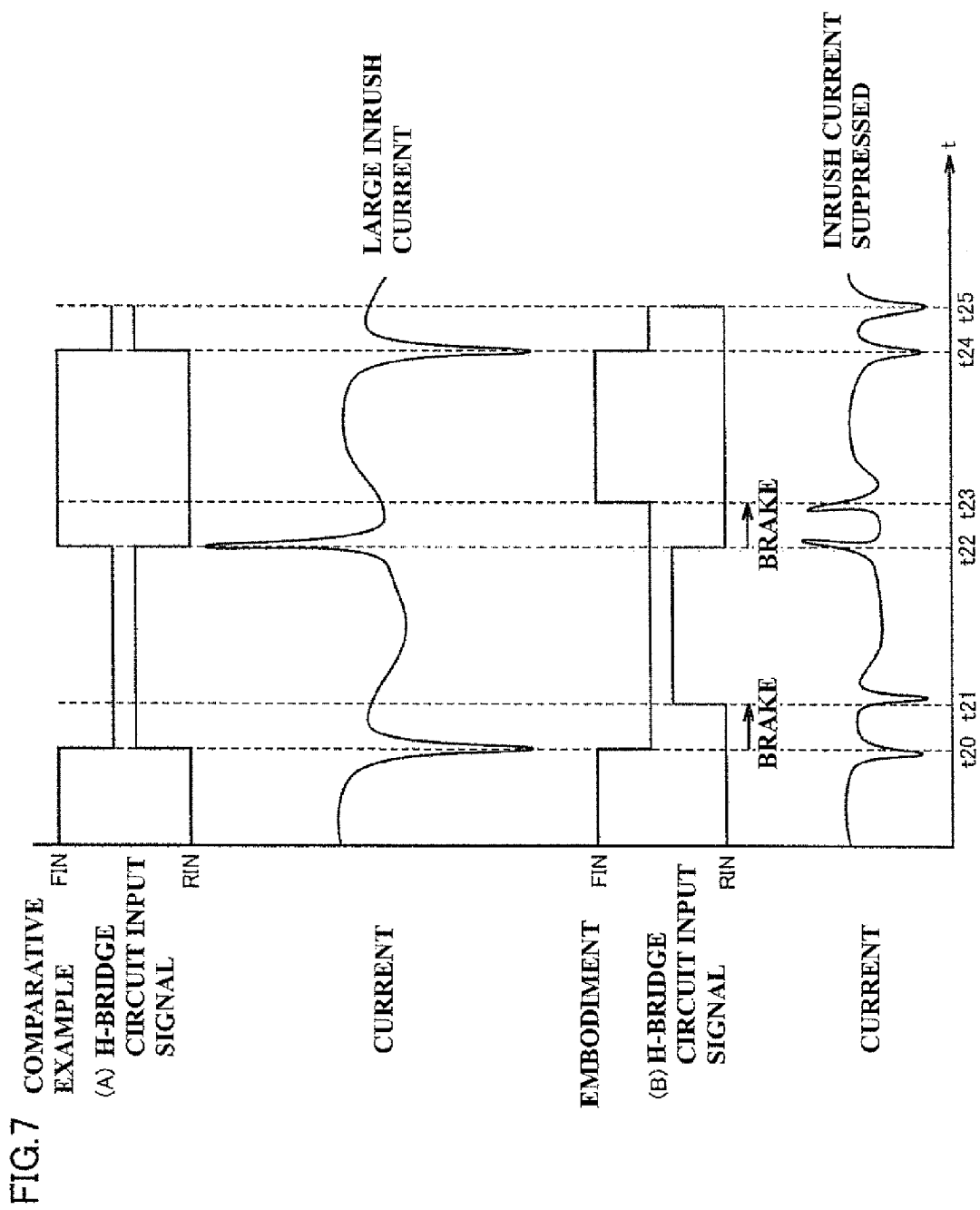
FIG. 7 is a diagram illustrating inrush current in the case where driving signals FIN and RIN are inputted into an H-bridge circuit.

FIG. 7 is a diagram illustrating inrush current in the case where the driving signals FIN and RIN are inputted into the H-bridge circuit.

FIG. 7(A) illustrates the waveform of a driving signal inputted into a conventional H-bridge circuit as a comparative example.

As shown in FIG. 7(A), the driving signals FIN and RLN have a complementary logic relationship, and thus the timing at which the driving signal FIN drops from H level to L level is essentially the same as the timing at which the driving signal RIN rises from L level to H level. There is thus a problem in that inrush current caused by the driving signal FIN dropping from H level to L level and inrush current caused by the driving signal RIN rising from L level to H level occur simultaneously, which increases the overall inrush current. There is a further problem in which the inrush current causes an excessive voltage drop.

FIG. 7(B) illustrates the waveform of a driving signal inputted into the H-bridge circuit according to the present embodiment.

FIG. 7(B) illustrates a case where the duty ratio has been adjusted so that the timings of the rise and fall of the driving signals FIN and RIN do not overlap. As a result, the fall of the driving signal FIN from H level to L level occurs at a time t20 while the rise of the driving signal RIN from L level to H level occurs at a time t21, and thus the respective timings are staggered, which in turn results in the inrush current caused by the fall of the driving signal FIN from H level to L level and the inrush current caused by the driving signal RIN rising from L level to H level occurring at staggered timings as well, and thus the overall inrush current can be suppressed. An excessive voltage drop can thus be suppressed by suppressing the magnitude of the inrush current.

Likewise, the fall of the driving signal RIN from H level to L level occurs at a time t22 while the rise of the driving signal FIN from L level to H level occurs at a time t23, and thus the respective timings are staggered, which in turn results in the inrush current caused by the fall of the driving signal RIN from H level to L level and the inrush current caused by the driving signal FIN rising from L level to H level occurring at staggered timings as well, and thus the overall inrush current can be suppressed.

This suppresses a drop in the cell voltage, which in turn makes it possible to maintain a state of high accuracy in the blood pressure measurement as well as extend the lifespan of the battery in the blood pressure meter.

Although the present embodiment describes a technique in which the respective duty ratios of the control signal (pulse signal) and inverted pulse signal outputted from the CPU 100 are adjusted in the signal conditioning circuit 63 and the driving signals FIN and RIN are outputted, it is also possible to adjust only one of the duty ratios.

Furthermore, although the present embodiment describes a case where the signals are adjusted using a NAND circuit, the embodiment is not particularly limited to a NAND circuit; the signals may be adjusted using another type of logic circuit, such as an AND circuit or a NOR circuit, or the configuration may employ a Schmitt trigger.

Figure 8:
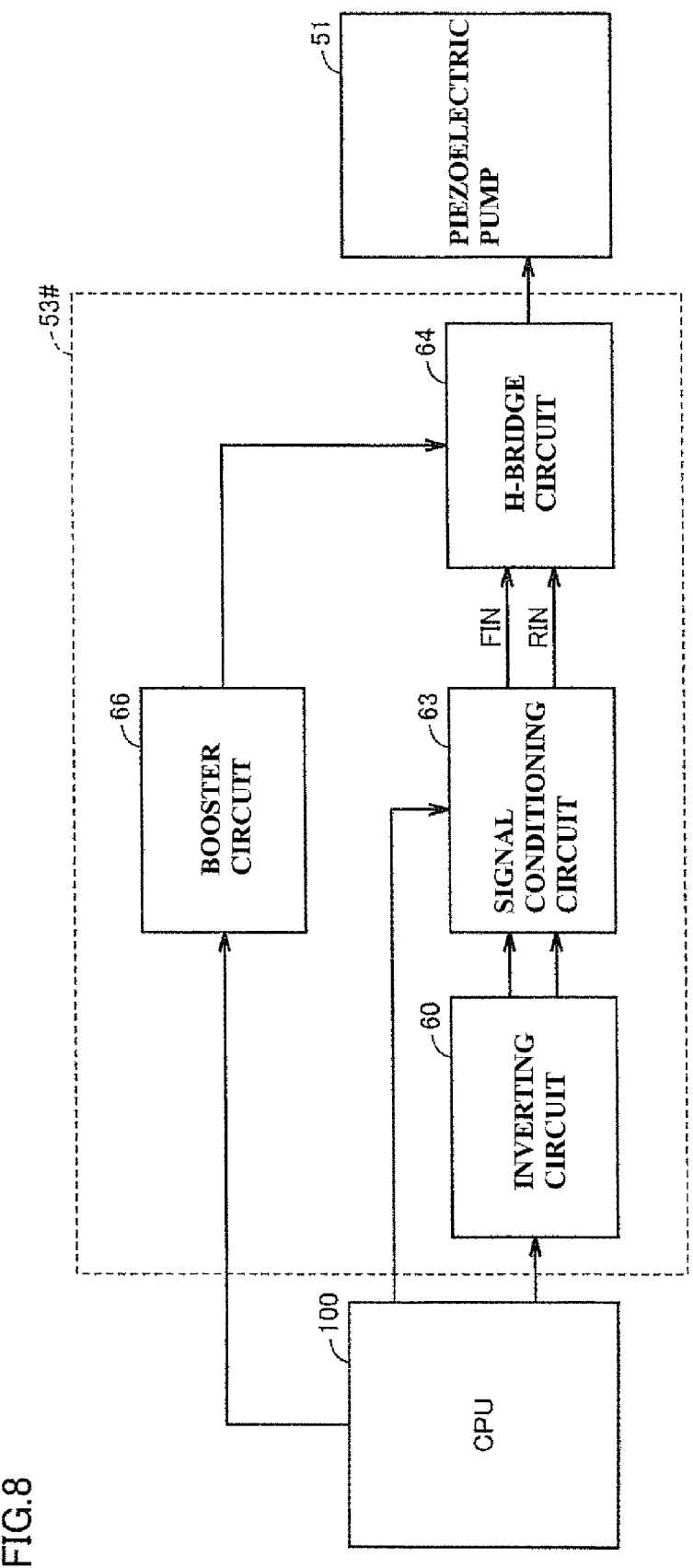
FIG. 8 is a diagram illustrating the configuration of a pump drive circuit 53# according to a variation on the embodiment of the present invention.

FIG. 8 is a diagram illustrating the configuration of a pump drive circuit 53# according to a variation on the aforementioned embodiment of the present invention.

As shown in FIG. 8, the pump drive circuit 53# differs from the pump drive circuit 53 shown in FIG. 3 in that the signal conditioning circuit 62 has been replaced with a signal conditioning circuit 63. The configuration is the same in other respects, and thus detailed descriptions thereof will not be repeated.

Figure 9:
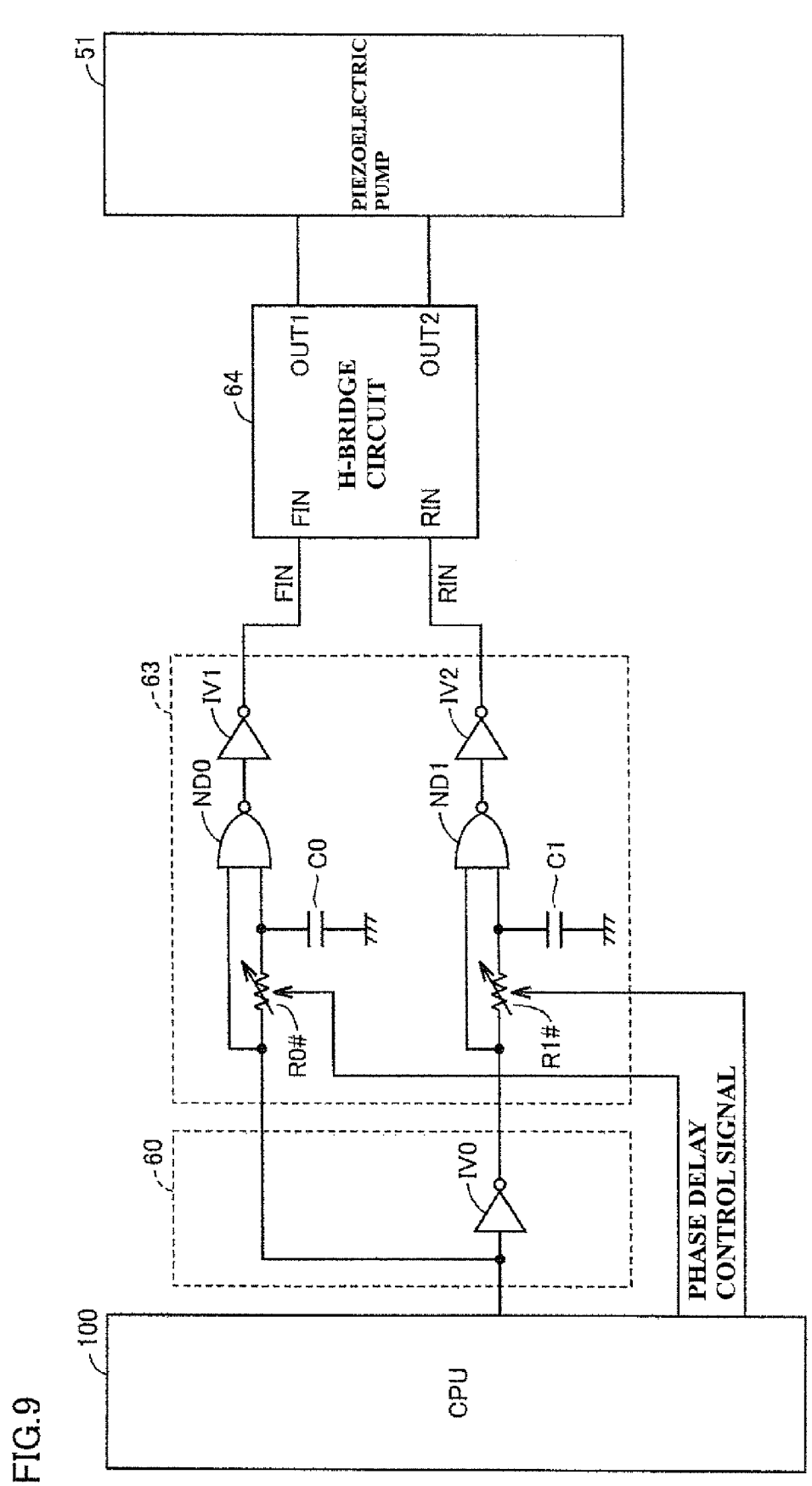
FIG. 9 is a diagram illustrating in detail the configuration of the inverting circuit 60 and a signal conditioning circuit 63 according to the variation on the embodiment of the present invention.

FIG. 9 is a diagram illustrating in detail the configuration of the inverting circuit 60 and the signal conditioning circuit 63 according to this variation on the aforementioned embodiment of the present invention.

As shown in FIG. 9, the signal conditioning circuit 63 differs from the signal conditioning circuit 62 in that the resistance elements R0 and R1 have been replaced with resistance elements R0# and R1#. The configuration is the same in other respects, and thus detailed descriptions thereof will not be repeated.

The resistance elements R0# and R1# are variable resistance elements, and the resistance values thereof change in accordance with a phase delay control signal from the CPU 100. Although the configuration in the present variation is such that the resistance values of both the resistance elements R0# and R1# change in accordance with phase delay control signals, note that it is also possible to adjust only one of the resistance values, or enable both resistance values to be adjusted independently. The selection of variable resistance or variable capacitance is changed depending on an arm circumference, a wrist circumference, remaining battery power, a looser wrap in the cuff, and so on.

By adjusting the resistance values, the rise to H level and the drop to L level of the aforementioned signal that has passed through the low-pass filter can be adjusted. In other words, fine adjustments can be made to the duty ratios of the driving signals FIN and RIN outputted from the signal conditioning circuit 63, and thus driving signals that match the properties of the piezoelectric pump can be inputted into the H-bridge circuit 64.

Although the present variation describes a case where variable resistance elements are used as the resistance elements R0# and R1#, the configuration is not limited to thereto; fine adjustments can also be made to the rise to H level and the fall to L level of the signal that has passed through the low-pass filter using a configuration in which the capacitance elements C0 and C1 are variable capacitance elements and the capacitance components are changed. Of course, a configuration in which the two are combined is also possible.

Meanwhile, with respect to the driving signals FIN and RIN, a technique in which the pulse signals from the CPU are outputted in a staggered manner can be considered; however, depending on the driving frequency of the piezoelectric pump, it is necessary to control time within 1 μsec, requiring a high-clock CPU, which consumes a large amount of power and shortens the lifespan of the battery. However, employing the present technique makes it possible to stagger the pulse signals using a simple system, which is advantageous in terms of both costs and the amount of power that is consumed.

The foregoing has described exemplary embodiments of the present invention, but it should be noted that the embodiments disclosed above are to be understood as being in all ways exemplary and in no way limiting. The scope of the present invention is defined by the scope of the appended claims, and all changes that fall within the same essential spirit as the scope of the claims are intended to be included therein as well.

REFERENCE SIGNS LIST 1 electronic blood pressure meter
10 main body portion
11 front cover
20 cuff
21 air bladder
31 cuff air tube
40 display unit
41 operation unit
41A measure/stop switch
41B timer set switch
41C memory switch
41D, 41E arrow switch
42, 43 memory
44 battery
45 timer
51 piezoelectric pump
52 valve
53 pump drive circuit
54 valve drive circuit
100 CPU (Central Processing Unit)
321 pressure sensor
331 oscillation circuit
335 adjustment circuit
1122 sensor abnormality detection unit

The invention claimed is:

1. An electronic blood pressure meter capable of suppressing inrush current, the electronic blood pressure meter comprising:
a cuff that is to be worn on a measurement area;
a piezoelectric pump that adjusts a pressure applied to the cuff;
a drive circuit that drives the piezoelectric pump; and
a controller that outputs, to the drive circuit, a pulse signal defining a driving timing of the piezoelectric pump,
wherein the drive circuit comprises:
an inverting circuit that outputs a non-inverted pulse signal having a same pattern as the pulse signal and an inverted pulse signal having an inverted pattern of the pulse signal;
a first signal conditioning circuit comprising a first delay circuit and a first waveform shaping circuit for processing the non-inverted pulse signal to produce a first driving signal such that timing of a rise of a positive going pulse in the first driving signal is delayed with respect to timing of a rise of a positive going pulse in the non-inverted pulse signal;
a second signal conditioning circuit comprising a second delay circuit and a second waveform shaping circuit for processing the inverted pulse signal to produce a second driving signal such that timing of a rise of a positive going pulse in the second driving signal is delayed with respect to timing of a rise of a positive going pulse in the inverted pulse signal so that the timings of a rise and fall of the first and second driving signals do not overlap; and a switching circuit that switches a current flow through the piezoelectric pump between a first direction and a second direction in response to the corresponding first and second driving signals.

2. The electronic blood pressure meter according to claim 1, wherein at least one of the first delay circuit and the second delay circuit comprises a variable capacitance element whose capacitance component changes in accordance with an instruction from the controller.

* * * * *